(12) United States Patent
Saha et al.

(10) Patent No.: US 9,248,942 B2
(45) Date of Patent: Feb. 2, 2016

(54) LIQUID PHASE EPOXIDATION PROCESS

(71) Applicant: South Bank University Enterprises Ltd, London (GB)

(72) Inventors: Basudeb Saha, London (GB); Krzysztof Ambroziak, Wierzchowo (PL); David C. Sherrington, Glasgow (GB); Rene Mbeleck, Paris (FR)

(73) Assignee: South Bank University Enterprises Ltd., London (GB)

( * ) Notice: Subject to any disclaimer, the term of this patent is extended or adjusted under 35 U.S.C. 154(b) by 0 days.

(21) Appl. No.: 14/277,335

(22) Filed: May 14, 2014

(65) Prior Publication Data

US 2014/0248006 A1    Sep. 4, 2014

Related U.S. Application Data

(62) Division of application No. 13/388,065, filed as application No. PCT/GB2010/001458 on Jul. 30, 2010, now Pat. No. 8,759,552.

(51) Int. Cl.
*B65D 30/06* (2006.01)
*B65D 33/00* (2006.01)
(Continued)

(52) U.S. Cl.
CPC ........... *B65D 33/00* (2013.01); *B01D 3/009* (2013.01); *B01J 19/32* (2013.01); *B01J 31/165* (2013.01);
(Continued)

(58) Field of Classification Search
CPC ......... B65D 33/00; B01D 3/009; B01J 19/32; B01J 31/165; B01J 31/1658; B01J 31/181; B01J 31/1815; B07B 1/46; C07D 301/19; C07D 303/06
USPC ........................................................ 383/117
See application file for complete search history.

(56) References Cited

U.S. PATENT DOCUMENTS

| 3,351,635 A | 11/1967 | Koller |
| 3,489,775 A | 1/1970 | de Roch et al. |

(Continued)

FOREIGN PATENT DOCUMENTS

| CN | 1534031 A | 10/2004 |
| EP | 0 623 389 A1 | 11/1994 |

(Continued)

OTHER PUBLICATIONS

International Search Report for corresponding International Application No. PCT/GB2010/001458 mailed Mar. 23, 2011.
(Continued)

*Primary Examiner* — T. Victor Oh
(74) *Attorney, Agent, or Firm* — Renner, Otto, Boisselle & Sklar, LLP

(57) ABSTRACT

The present invention provides a continuous process for the epoxidation of an olefinic compound with an oxidant, which process comprises reaction of an olefinic compound with an oxidant in the presence of a catalyst in an apparatus that comprises a reactive distillation column, which column comprises
 (i) a reactive section, which comprises the catalyst
 (ii) a rectifying section situated above the reactive section and adapted to allow separation of reagents and/or by-products from products
 (vii) a stripping section situated below the reactive section and adapted to allow
separation of product from reagents and/or by-products
 (viii) a vessel situated below the stripping section and adapted to provide a source of heat for the column and in which initial vaporization of one or more of the reagents can occur,
wherein the temperature in the reactive section (i) is a temperature at which the reaction between the olefinic compound and the oxidant takes place and the temperature in the stripping section (iii) is higher than the temperature in the rectifying section (ii).

6 Claims, 7 Drawing Sheets

(51) Int. Cl.
*B01D 3/00* (2006.01)
*B01J 19/32* (2006.01)
*B01J 31/16* (2006.01)
*B01J 31/18* (2006.01)
*B07B 1/46* (2006.01)
*C07D 301/19* (2006.01)
*C07D 303/06* (2006.01)

(52) U.S. Cl.
CPC ............ *B01J 31/1658* (2013.01); *B01J 31/181* (2013.01); *B01J 31/1815* (2013.01); *B07B 1/46* (2013.01); *C07D 301/19* (2013.01); *C07D 303/06* (2013.01); *B01J 2208/00814* (2013.01); *B01J 2219/32279* (2013.01); *B01J 2219/32408* (2013.01); *B01J 2219/32466* (2013.01); *B01J 2219/32483* (2013.01); *B01J 2231/72* (2013.01); *B01J 2523/69* (2013.01); *B01J 2531/16* (2013.01); *B01J 2531/46* (2013.01); *B01J 2531/56* (2013.01); *B01J 2531/64* (2013.01); *B01J 2531/66* (2013.01); *B01J 2531/72* (2013.01); *B01J 2531/821* (2013.01); *B01J 2531/842* (2013.01)

(56) References Cited

U.S. PATENT DOCUMENTS

| | | |
|---|---|---|
| 3,526,645 A | 9/1970 | Vangermain et al. |
| 4,215,011 A | 7/1980 | Smith, Jr. |
| 4,443,559 A | 4/1984 | Smith, Jr. |
| 4,828,719 A | 5/1989 | Katinger |
| 4,845,252 A | 7/1989 | Schmidt et al. |
| 5,266,546 A | 11/1993 | Hearn |
| 5,420,313 A | 5/1995 | Cunnington et al. |
| 5,807,803 A | 9/1998 | Cunnington et al. |
| 5,942,456 A * | 8/1999 | Crossland et al. ............... 502/2 |
| 6,337,412 B1 | 1/2002 | Gelbein |

FOREIGN PATENT DOCUMENTS

| | | |
|---|---|---|
| GB | 114896 | 4/1918 |
| GB | 2 034 597 A | 6/1980 |
| WO | 97/11072 | 3/1997 |
| WO | 98/25696 | 6/1998 |

OTHER PUBLICATIONS

Written Opinion of the International Searching Authority for corresponding International Application No. PCT/GB2010/001458 mailed Mar. 23, 2011.

Sharpless et al., "Metal-Catalyzed, Highly Selective Oxygenations of Olefins and Acetylenes with *tert*-Butyl Hydroperoxide. Practical Considerations and Machanisms." Aldrichimica Acta, vol. 12, No. 4, 1979, pp. 63-74.

Ambroziak et al., "Investigation of Batch Alkene Epoxidations Catalyzed by Polymer-Supported Mo(VI) Complexes", Ind. Eng. Chem. Res. vol. 48, No. 7, 2009, pp. 3293-3302.

Mbeleck et al., "Stability and recycling of polymer-supported Mo(VI) alkene epoxidation catalysts", ScienceDirect, Reactive & Functional Polymers, vol. 67, 2007, pp. 1448-1457.

Communication pursuant to Article 94(3) EPC for corresponding Application No. EP 10 749 674.7 dated Feb. 22, 2013.

First Office Action issued in corresponding Chinese Application No. 201080044175.2 dated Nov. 4, 2013 and English translation.

Second Office Action issued in corresponding Chinese Application No. 201080044175.2 dated Jun. 10, 2014 and English translation.

* cited by examiner

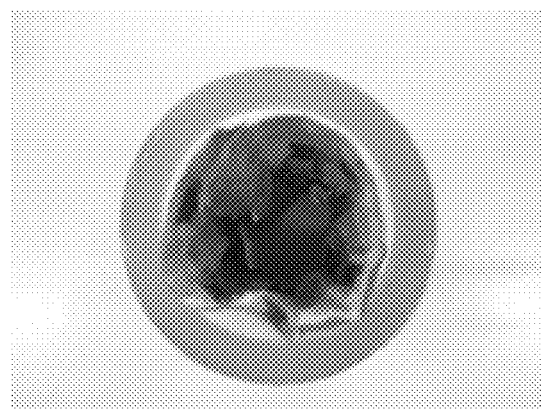
Figure 3
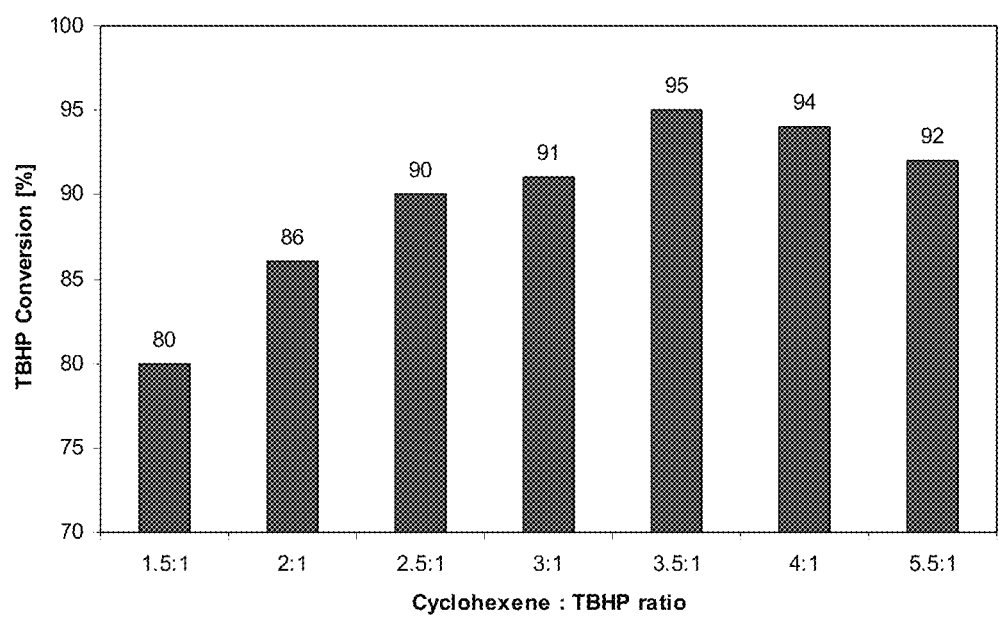

LIQUID PHASE EPOXIDATION PROCESS

This application is a divisional of U.S. patent application Ser. No. 13/388,065 filed on Jan. 31, 2012, which is a 371 of PCT/GB2010/001458 filed on Jul. 30, 2010 and claims priority to United Kingdom No. 0913318.2 filed on Jul. 31, 2009, which are hereby incorporated herein by reference in their entirety.

The present invention relates a process for the continuous epoxidation of olefinic compounds and to apparatus for use in that process.

Epoxides are versatile and useful intermediates in organic synthesis. The epoxidation of olefinic compounds is a well known process which is operated industrially. For example, the use of a soluble molybdenum catalyst or a heterogeneous titanium/silica catalyst for the epoxidation of propylene to propylene oxide using alkyl hydroperoxide is known.

An industrial example of the use of Mo(IV) complexes is the Halcon Process, which uses a soluble Mo complex to catalyse the formation of propylene oxide from propylene highly selectively in the liquid phase at 373 K. This process is described in U.S. Pat. No. 3,351,635.

Currently, many epoxidation reactions can only be performed using batch reactions, which can limit the scope of the reaction. Problems associated with large scale batch reactions when compared to smaller laboratory based reactions include reduced efficiency, use of large quantities of solvents, temperature control issues, high unit cost and use of large quantities of potentially explosive oxidants such as peracid oxidants, which is both potentially dangerous and also potentially harmful to the environment.

U.S. Pat. No. 5,420,313 describes the use of polymer supported molybdenum, tungsten, vanadium and titanium complexes in the conversion of olefinic compounds to their epoxide in the presence of a peroxide.

The listing or discussion of an apparently prior-published document in this specification should not necessarily be taken as an acknowledgement that the document is part of the state of the art or is common general knowledge However, despite the success with immobilised catalysts in small scale epoxidation reactions, there have been no significant attempts to provide medium to large scale production using this technology. Reasons for this include the concern that in continuous processes apparently long-lived heterogeneous catalysts may prove to be unstable, with even low levels of metal leaching causing problems.

Therefore there is a need for an epoxidation process which does not result in the polymer supported catalyst becoming unstable.

Further, there remains a need to provide alternative epoxidation processes which can be performed on a large scale and which avoid one or more of the problems associated with large scale batch reactions.

It is an object of the invention to solve one or more of these problems.

The present invention provides a continuous process for the epoxidation of olefins, for example alkenes and terpenes. In this process the olefinic compound is reacted with an oxidant in the presence of a polymer supported catalyst in a reactive distillation column.

More particularly, the present invention provides a continuous process for the epoxidation of an olefinic compound with an oxidant, which process comprises reaction of an olefinic compound with an oxidant in the presence of a catalyst in an apparatus that comprises a reactive distillation column, which column comprises
(i) a reactive section, which comprises the catalyst
(ii) a rectifying section situated above the reactive section and adapted to allow separation of reagents and/or by-products from products
(iii) a stripping section situated below the reactive section and adapted to allow
separation of product from reagents and/or by-products
(iv) a vessel situated below the stripping section and adapted to provide a source of heat for the column and in which initial vaporisation of one or more of the reagents can occur,
wherein the temperature in the reactive section (i) is a temperature at which the reaction between the olefinic compound and the oxidant takes place and the temperature in the stripping section (iii) is higher than the temperature in the rectifying section (ii).

The present invention also provides an apparatus in which the continuous liquid phase epoxidation of an olefinic compound with an oxidant can take place. This apparatus comprises a reactive distillation column, which column comprises
(i) a reactive section, which is adapted so that it can contain the catalyst
(ii) a rectifying section situated above the reactive section and adapted to allow separation of reagents and/or by-products from products
(v) a stripping section situated below the reactive section and adapted to allow
separation of product from reagents and/or by-products
(vi) a vessel situated below the stripping section and adapted to provide a source of heat for the column and in which initial vaporisation of one or more of the reagents can occur.

As used herein, when we refer to "products" we mean the desirable products of the reaction. Undesirable products are referred to as "by-products".

The inventors have surprisingly found that the use of a polymer-supported molybdenum catalyst in a reactive distillation column can provide efficient and selective epoxidation of olefinic compounds such as alkenes and terpenes.

Catalyst compositions suitable for use in the process of present invention include those comprising one or more metals complexed to an organic or inorganic support through the intermediacy of a ligand such as a nitrogen based ligand molecule, for example an imidazole ligand. Suitable catalysts include those comprising at least one of titanium, vanadium, molybdenum, tungsten, manganese, iron, ruthenium and copper. Preferably the catalyst composition comprises at least one of molybdenum, titanium, vanadium and/or tungsten. Most preferably the catalyst comprises molybdenum. More than one metal may be present in the catalyst composition.

Suitable catalysts include those described in U.S. Pat. No. 5,420,313.

The catalyst is typically complexed to an organic or inorganic support through the intermediacy of an imidazole ligand. The imidazole ligand may comprise unsubstituted imidazole or a substituted imidazole such as 2-pyridyl-2-imidazole, benzimidazole, 5-5'-bibenzimidazole, carboxylic acid and hydroxyl substituted imidazoles and benzimidazoles. The imidazole ligand may be attached to the support through any part of the imidazole or substituted imidazole provided that the imidazole ring is available for complexing to the metal of the catalyst. The imidazole ligand may comprise part of the support rather than being pendant thereto; for example the imidazole may comprise part of a polymer repeating unit.

A preferred class of polymers for use in the catalysts used in the present invention are polybenzimidazoles, such as poly[2,2'(m-phenylene)-5,5'-bibenzimidazole], which is a polymer having a repeating unit represented by the formula (I). In a preferred aspect of the invention the catalyst is a polybenzimidazole supported catalyst. It is preferred that the polybenzimidazole is poly[2,2'(m-phenylene)-5,5'-bibenzimidazole].

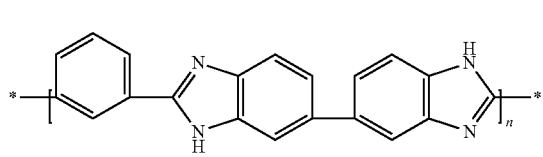

(I)

If an organic support is used it may be any suitable polymer such as one which is stable under the reaction conditions used in the process of the invention. Suitable polymer supports include but are not limited to styrene polymers, methacrylate polymers, glycidyl methacrylate polymers, benzimidazole polymers, polyimides, polybenzothiazoles, polybenzoxazoles and optionally copolymers with suitable co-monomers, optionally the polymers may be cross-linked.

The support may comprise a functionalised inorganic support such as functionalised silica or alumina.

Preferably the support comprises benzimidazole.

An example of a suitable catalyst support is polystyrene 2-(aminomethyl)pyridine.

As described in U.S. Pat. No. 5,420,313, the catalyst composition may be prepared by effecting a ligand exchange reaction between an organometallic complex of a metal as listed above having a suitable leaving group with a support having a nitrogen based ligand, such as imidazole.

The catalyst used in the process of the present invention may be activated before use by oxidising with a suitable oxidant, such as a peroxide, or the catalyst may be oxidised 'in situ' by reaction with the oxidant, such as a peroxide reactant.

The olefinic compound for use in the process of the present invention may be any organic olefinic compound having at least one olefinic double bond having the general formula (II).

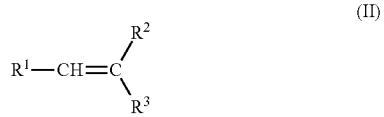

(II)

Wherein $R^1$, $R^2$ and $R^3$ can be the same or different, substituted or non-substituted and are each independently selected from hydrogen, alkyl, akenyl, aryl, alkaryl, cycloalkyl or alkylcycloalkyl, hydrocarbyl groups. Preferably, $R^1$, $R^2$ and $R^3$ each have less than 30 carbon atoms. More preferably $R^1$, $R^2$ and $R^3$ each have no more than 14 carbon atoms.

In addition any of $R^1$ $R^2$ or $R^3$ can be linked together to form a substituted or non-substituted ring structure, such as cycloalkyl, cycloalkenyl or alkylcycloalkyl, cyclic hydrocarbyl group, preferably having no more than 14 carbon atoms in total. In a preferred aspect of the invention the ring contains from 5 to 12 carbon atoms.

The olefinic compound may be straight-chain, branched-chain or cyclic. Cyclic olefinic compounds include monocyclic, bicyclic or polycyclic. The olefinic compound may be mono-olefinic, di-olefinic or poly-olefinic. If more than one olefinic bond is present the compound may be conjugated or non-conjugated. The olefinic compound may be substituted by one or more of a halide (e.g. Cl, F, Br, I), an ether group, an ester group and/or an allylic hydroxyl. The olefinic compound may be a vinyl ester, phenyl or nitrile compound. If substituted by one or more electron withdrawing groups these should not be substituted directly on the olefinic double bond but should be remote therefrom (i.e. at the closest on the carbon alpha to the olefinic bond, preferably more carbons removed from the olefinic bond).

Examples of olefinic compounds which may be used in the present invention include but are not limited to hexenes, octenes, decenes, dodecenes, cyclohexenes, styrenes, methylenecyclohexanes and terpenes. Specific examples of olefinic compounds which may be used include but are not limited to dicyclopentadiene, hexadiene, 4-vinylcyclohexene, limonene, cyclooctadiene and cyclohexene.

In the process of the present invention the oxidant is typically in the form of a peroxide. Any suitable peroxide may be used, for example hydrogen peroxide, an organic hydroperoxide, for example an alkyl hydroperoxide or a peroxide ether. Preferably the oxidant is an alkyl hydroperoxide, such as tert-butyl hydroperoxide, cumene hydroperoxide, ethylene hydroperoxide or hydrogen peroxide. Most preferably the peroxide is tert-butyl hydroperoxide (TBHP).

The process of the present invention may be performed in neat liquid reagents or a solvent may be used. It is preferred that the process of the invention is conducted in the absence of solvent other than that associated with the oxidants. For safety reasons the oxidant is typically used in the form of a solution. For example, TBHP is explosive and is not very stable when neat.

Examples of suitable solvents, which may be used if necessary, include aromatic, alcohol, alkane, ester, ketone or halogenated solvents. Solvents such as 1,2 dichloromethane and toluene are preferred. Water can be tolerated, typically in an amount of no more than 30% based on the oxidant.

The process of the present invention is typically performed at about atmospheric pressure.

The process of the invention may be performed at any suitable temperature depending on the reagents, catalysts and solvents used. The process of the invention is typically carried out at a temperature range of from 20 and 500° C. The reaction takes place in the reactive section of the reactive distillation. Thus, the temperature in the section of the column is typically in the range of from 20 and 500° C., for example 40 to 200° C. Preferably the reaction temperature in the reactive section of the column does not exceed the boiling point of the oxidant used.

The actual temperature required in the reactive section will depend on the volatility of the reagents used and will be known to the person skilled in the art.

In the process of the invention the molar ratio of the olefinic compound to the oxidant is typically in the range of 0.5:1 to 100:1, preferably 1:1 to 20:1, more preferably the molar ratio of olefinic compound to oxidant is about 3.5:1.

The amount of catalyst that is used will depend on the scale of the reaction.

In accordance with the present invention the epoxidation process is carried out using reactive distillation. Reactive distillation (RD) is a unit operation which combines simultaneous chemical reaction and multi-component distillation in the same vessel in a single step.

The reactive distillation column used in the present invention comprises four essential parts: (i) a reactive section, (ii) a rectifying section, (iii) a stripping section and (iv) a vessel, alternatively referred to as a reboiler.

The reactive section is the section of the reactive distillation column in which the epoxidation reaction takes place. The catalyst is placed in this section of the column.

Preferably, the catalyst is held in the reactive section by means of a permeable particle container, also known as a "catalyst packing". Any suitable catalyst packing can be used to retain the catalyst in the reactive section of the column. For example, catalyst packing such as known "envelope shaped" packing may be used. An example of this type of packing is KATMAX™ sold by Koch-Glitsh. The present inventors have developed a new "rolled belt shaped" catalyst packing which is suitable for use in the process of the present invention.

The rolled belt shaped catalyst packing can be used to retain any catalyst and its potential uses are not restricted to use in the process of the present invention. This catalyst packing is particularly suitable for use with reusable catalysts.

Another aspect of the present invention is to provide a "rolled belt shaped" catalyst packing (permeable particle container) suitable for containing a catalyst such as a catalyst described above. By suitable catalyst it is meant that the average catalyst particle size is equal to or greater than 0.03 mm. For example from about 0.03 mm to about 2 mm, e.g. from about 0.03 mm to 0.06 mm or 0.14 mm.

The "rolled belt shaped" catalyst packing comprises a belt of mesh. The mess size, i.e. the size of the holes or spaces in the mesh is selected depending on factors such as the form and size of the catalyst. The mesh size is typically less than 0.1 mm, although it is envisaged that for some applications larger mesh sizes could be used. For use in the the epoxidation process of the present invention, the mesh size is typically from about 0.01 mm to about 0.05 mm, for example 0.02 mm, 0.03 mm or 0.04 mm. Typically, the size of the mesh is smaller than the particle size of the catalyst.

The belt typically comprises two sheets of mesh. These sheets are typically approximately the same size. The two sheets of mesh are initially joined together by soldering along three edges. The catalyst is then placed between the two layers of mesh and the remaining edge is then soldered to seal the layers of mesh together. It will be appreciated that the same effect could be obtained by folding a single mesh sheet and soldering two edges before adding the catalyst and then once the catalyst has been added, sealing the remaining edge.

Soldered stripes can optionally be placed on the belt to allow good contact of liquid with the catalyst. Once the belt is packed with the catalyst, the soldered stripes give some curvature to the mesh belt by providing chambers in the belt which when filled with catalyst create protrusions, which increases the contact time of the liquid with the catalyst in the reactive section of the column.

Preferably the stripes are soldered on the belt between 1 and 3 cm apart. The stripes may be placed in any suitable configuration on the belt. In one preferred configuration the stripes are placed so their longer side is parallel to the shorter sides of the belt. The length of each stripe is typically less than the length of the short sides of the belt. For example, the stripes may have a length that is from about a quarter to a third the length of the shorter side of the belt. Typical dimensions for the stripes are about 0.005 m wide and about 0.020 to 0.025 m in length. The size of the stripes does not typically depend on the size of the belt. The soldered stripes are soldered onto the belt using solder alloy. Preferably the solder alloy consists of Pb 93.5% Sn 5% Ag 1.5% with a melting range between 296 and 301° C. However, it would be envisaged that if the process is to be carried out at a higher temperature than the above-mentioned alloy melting range then an appropriate high melting point solder alloy or braze alloy could be used instead.

The rolled belt can be made of any material which is resistant to organic chemicals and elevated temperatures. Suitable materials are those that have sufficient resilience so that the catalyst is held in place between two pieces of mesh and also have sufficient flexibility to allow the belt to be rolled to the diameter required for it to fit within the reaction vessel in which it is used. Examples of suitable materials which can be used include Teflon and stainless steel. In a preferred aspect of the present invention the rolled belt is made of stainless steel. The rolled belt shaped packing material is typically used to hold the catalyst only. It is preferable that the belt is thin.

Typically, the rolled belt catalyst container of the invention does not require a longitudinal support to hold it in place in the reaction vessel in which it is used, such as the reactive section of a reactive distillation column.

As an example of the use of the permeable particle container described above, it may be used in the epoxidation reaction of the invention. For use in this process the permeable particle container is packed or filled with the catalyst and sealed closed so that the catalyst is held in the permeable particle container. The permeable particle container or belt containing the catalyst is then rolled to a suitable diameter so that it fits in the reactive section of the reactive distillation column.

The permeable particle container of the present invention is particularly suitable for use in liquid phase reactions. The inventors have surprisingly found that that the permeable particle container helps to provide optimum residence time in the reactive section of for example a reactive distillation column and this achieve high conversion of the reactants to the desired product. It has also be found that this arrangement can provide maximum concentration of the reactants in the reactive section of the reactive distillation column and minimum concentration of the product in the reaction section of the reactive distillation column and that this can help reduce by-product formation. The permeable particle container can also provide optimum liquid hold up in the column for the liquid phase reaction. Without wishing to be bound by theory, it is believed that these advantages are due to the structure of the permeable particle container, for example the rolled belt arrangement and the way in which the catalyst material is packed.

In one aspect of the process of the catalyst is held within a permeable particle container. For example, in a permeable particle container as described above, particularly the rolled belt permeable particle container described above.

The rectifying section is situated above the reactive section and allows for the separation of reactants and/or by-products from the desired products. Typically the products have a higher boiling point than the reactants (reagents) and/or the by-products. Thus, the reagents, by-products and products can be referred to as low boiling reactants and higher boiling products. In this context, the terms "low" and "higher" do not place any particular numerical limit on the boiling points to which they refer. These terms are simply used to indicate that the boiling point of one material is higher than that of another.

The rectifying section can be connected to a condenser. In a preferred aspect of the invention the rectifying section is situated below a condenser to condense and therefore re-circulate the reagents, preventing the loss of the reagents as vapour.

The stripping section allows for higher boiling point products to be separated from lower boiling point reagents and/or by-products. The stripping section is typically heated from the vessel (reboiler). Preferably the stripping section is maintained at a temperature such that any reagents present in the stripping section are at least in part int eh vapour phase. The temperature of the stripping section will be maintained at a level which is higher than that in the rectifying section. Preferably, the stripping section is insulated.

The stripping section is located under the reactive section.

The reactive distillation column further comprises one or more inlet ports for introduction of the reagents into the apparatus and/or one or more outlet ports for removing products from the apparatus.

The vessel (iv) or reboiler provides a source of heat for the column and is the vessel in which initial vaporisation of one or more of the reagents takes place. The reboiler can also receive the higher boiling point product which has been separated in the stripping section.

Typically the reboiler (vessel (iv)) has two ports, one adapted for loading the liquid components into the reboiler and another port at the bottom of the reboiler which is adapted for withdrawing the products during the process. The port for loading liquid components into the reboiler may be above the port for withdrawing products. For example, the port for loading liquid components may be at the top, or at least in the upper half of the reboiler and the port for withdrawing products may be at the bottom, or at least in the lower half of the reboiler.

Typically the reboiler is supplied with heat. Any suitable heat source can be used. For example, a steam generator may be used. Alternatively, an oil bath or an electrical heat source can be used. The temperature of the reboiler will be determined by the energy required to vaporise the reagents and distribute the vapour along the length of the column. The temperature will therefore depend on the reagents used and the size of the column. The temperature of the reboiler is typically higher than the temperature of other sections of the column. This is because the reboiler is constantly supplied with heat (e.g. via a steam generator or by an oil bath), whilst the other sections are heated by the vapour of the boiling mixture.

In the process of the invention it is preferred that heat is supplied to the reboiler in the form of steam. The temperature of the reboiler can be the same or different to that of the reactive section. For example in the epoxidation of limonene, the reactive section may be at a temperature of from 50 to 100° C. and the reboiler at a temperature of 175° C.

In the reactive section, the reaction takes place in the liquid phase. The epoxidation reaction takes place in the liquid phase when the reagents pass over or through the heterogeneous catalyst.

The sections of the reactive distillation column can be connected to one another using any suitable means. For example, the reactive section may be connected to other sections of the column via one or more metal plates. In a preferred aspect of the invention the plates are made of stainless steel. If necessary, to avoid any leakage appropriate gaskets may be placed between the plate and the column. It is preferred that the gaskets used in the present invention are Teflon, although other gaskets may be used providing they are stable to the process of the reaction and the reaction temperature. Each plate may have one or more inlet ports attached to it. The ports can be used for the introduction of reagents into the column. In an aspect of the present invention, one plate is present between the reboiler and the stripping section, one between the stripping section and the reactive section, one between the reactive section and the rectifying section and one between the rectifying section and the condenser. This arrangement allows for four potential points for the introduction of the reagents i.e. bottom of the striping section (SS), bottom of the reactive section (RS), top of reactive section (RS) and bottom of the rectifying section (RFS).

The reagents, the olefinic compound and the oxidant can be introduced into the reactive distillation column at any suitable location. The reagents can be pre-mixed before introduction into the reactive distillation column or may be introduced separately. Combinations of the pre-mixing and separate introduction of the reagents can be used.

As explained above, the apparatus used in the invention comprises at least one inlet port for introduction of the reagents into the apparatus. The apparatus may comprise two or more inlet ports.

The position of the inlet ports which will be used for the introduction of the oxidant and olefinic compound into the column can be varied depending on the reagents being used and factors such as their relative volatilities. Possible positions for the inlet ports include, but are not limited to, a position above the reactive section or below the reactive section. If there is more than one inlet port these can be positioned together or apart. It will be appreciated that the optimum locations will depend on the nature of the reagents. As an example the inlet port for the oxidant may be positioned at the top of the rectifying section and the inlet port for the olefinic compound may be positioned at the bottom of the stripping section.

Typically the inlet ports of the lower boiling point reagent would be below the inlet point of the higher boiling point reagent.

Typically the reagents are fed to the inlet ports through tubing. Any suitable tubing which is not reactive with the reagents can be used. For example polytetrafluoroethylene (PTFE) tubing can be used.

Typically, a means for controlling the rate of introduction of the reagents is provided. For example, the rate of flow may be controlled by a pump. Any suitable pump such as a peristaltic pump may be used. In a preferred aspect of the invention the flow rate is from 0.5 ml/min to 5 ml/min, preferably the operating flow rate of the reaction is about 1 ml/min. It will be appreciated that this will depend on the size of the column, the volume of the reactive section and the amount of catalyst.

The diameter of each section of the column will vary depending on the scale of the reaction. For example the diameter of each section of the column may be, but not limited to, from about 0.020 m to about 0.050 m. For example, for larger reactions the column diameter may be in the range of from about 0.2 to about 0.6 m.

The whole column or individual sections may or may not be insulated. In a preferred aspect the whole column is insulted. Any insulation know to those skilled in the art may be used, for example Superwool 607™ MAX blanket.

In one aspect, the present invention provides a process wherein:
(i) a proportion of the reagents is placed in the vessel (iv) and heated to a temperature where vaporisation occurs, and
(ii) the reagents from the vessel (iv), in the form of vapour, rise through the column heating the sections of the column, and
(iii) when the column reaches a steady state temperature, inlet ports are opened to allow the continuous flow of the reagents into the column at the same rate as the product is removed from the vessel (iv).

In the figures:
FIG. 1 shows an example of a reactive distillation column of the type used in the present invention.
FIG. 2 shows the rolled belt shaped catalyst packing FIG. 3 shows the percentage conversion of TBHP in the process of the present invention using the reactive distillation column dependant on the ratios of cyclohexene to oxidant.

Figure 1:
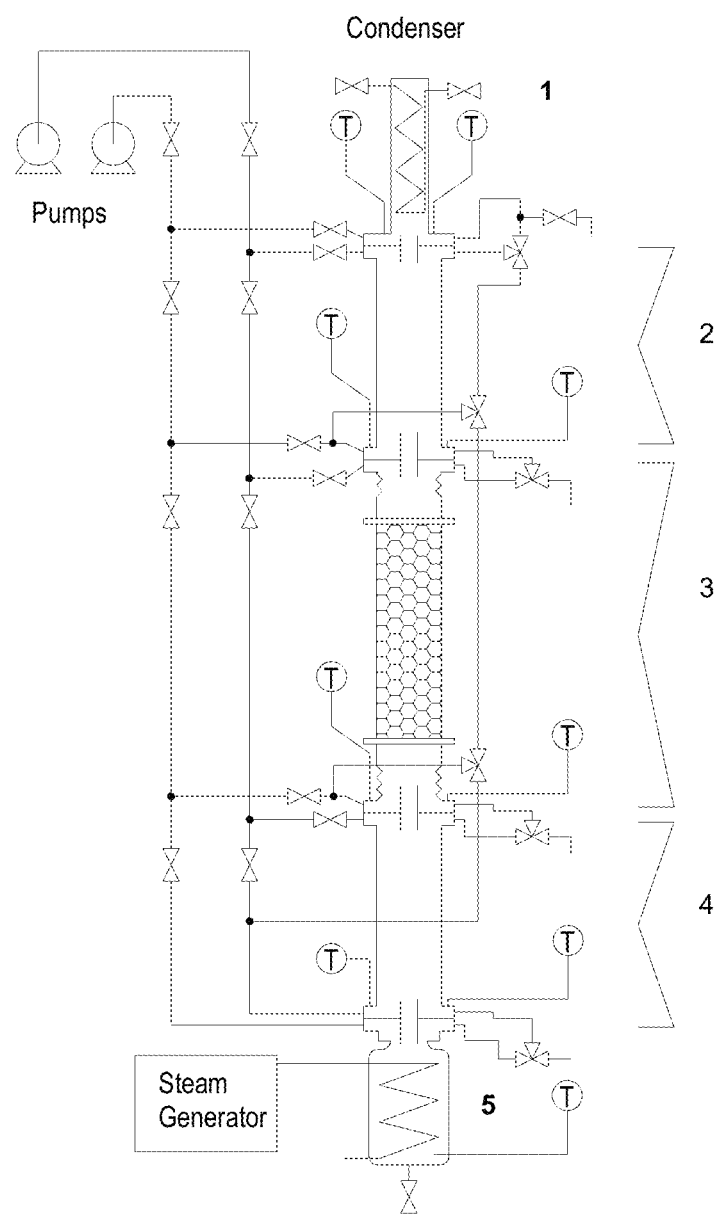

The reactive distillation column as shown in FIG. 1 comprises a condenser (1), a rectifying section (2), a catalytic reactive section (3), a stripping section (4), a reboiler (5), a steam generator (6), thermocouples (T) and inlet ports (7) and (8) for introducing into the reactive distillation column the oxidant and olefin independently and via peristaltic pumps (9) and (10), which are calibrated to control the flow rate of the reactants.

It is preferred that both reagents are at least initially introduced into the reboiler at room temperature. The reagents are then heated in the reboiler. When the liquids start to vaporise and the vapours move up the column, the temperature of the column increases until the reactive distillation column reaches total reflux. When the temperature of the reactive distillation column reaches steady state, the reactants can be introduced to the column at specified locations via inlet ports (7) and (8).

The temperature in the reactive section will depend on the boiling point of the reagents used and is held at such a temperature to maintain the olefin in the vapour phase and the oxidant at least partially in the vapour phase.

The reflux temperature will vary depending on the reagents used. For example the temperature in the reactive section may be held at about 80° C. for certain combinations of reagents. It is important that the temperature of the reactive section is monitored as this is the temperature at which the reaction takes place. The temperature in the other sections of the column can also be monitored. This will give information on the functioning of the system as a whole. It is also important as the temperatures in these sections will indicate when a steady state has been reached.

The resultant product epoxide will have a higher boiling point than the starting reagents and typically the boiling point of the product will be higher than that of any by-products. The product epoxide can then be removed from the bottom of the reboiler in the form of a liquid as it has a higher boiling point than either the starting olefinic compound or the oxidant.

The present invention will be explained in more detail with specific reference to the epoxidation of cyclohexene with TBHP.

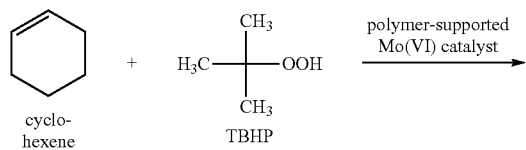

-continued

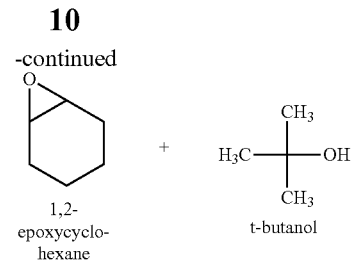

1,2-epoxycyclohexane + t-butanol

The PBI.Mo catalyst is prepared as described in U.S. Pat. No. 5,420,313 and then added to the 'rolled belt shaped' catalyst packing. The packing is then placed into the reactive section of the reactive distillation column. The initial reaction mixture in the reboiler is then heated to about 100° C. which causes the reagents to reflux, resulting in both reagents entering the vapour phase and passing through the reactive section containing the catalyst. After about 30 minutes the temperature of the column reaches steady state and the temperature reaches about 74° C. at the bottom and about 71° C. at the top of the reactive section (this temperature might vary depending of the TBHP:cyclohexene ratio). TBHP is then fed into the rectifying section of the column above the reactive section. Cyclohexene is simultaneously fed into the stripping section of the column below the reactive section. The molar ratio of the TBHP and cyclohexene feeds is preferably about 1:3. The product epoxycyclohexane can be continuously withdrawn from the bottom of the reboiler as a liquid.

Another example is the epoxidation of limonene with TBHP.

limonene + TBHP →(polymer-supported Mo(VI) catalyst)

limonene 1,2-epoxide + t-butanol

The reactive distillation column is set up as previously described. The initial reboiler mixture of TBHP and limone is then heated to about 180° C. which causes the reagents to reflux, resulting in both reagents entering the vapour phase and passing through the reactive section containing the catalyst. After about 30 minutes the temperature in the column reaches steady state and the temperature reaches about 80° C. at the bottom of the reactive section and about 77° C. at the top of the reactive section (these temperatures might slightly vary depending on the TBHP:limonene ratio). TBHP is then fed into the stripping section of the column below the reactive section of the column. Limonene is simultaneously fed at the top of the reactive section. The molar ratio of the TBHP and limonene feeds is preferably about 1:3. The product limonene 1,2-epoxide can be continuously withdrawn from the bottom of the reboiler as a liquid.

The present inventors have surprisingly found some significant and unexpected advantages associated with conducting epoxidation reactions in the manner used in the present invention. These advantages can include one of more of the following:

Higher levels of conversion can be achieved in comparison to batch reactions, side reactions and by-product production can be reduced, improvements in selectivity can be achieved, the amount of catalyst required to produce the same degree of conversion can be reduced when compared to batch processes, and processing advantages such as easier temperature control and eliminating the use of large quantities of flammable solvents can be obtained.

These and other advantages can lead to reduced production costs.

The invention is illustrated by the following non-limiting Examples.

Preparation of Catalyst Composition (PBI.Mo Catalyst)

A catalyst composition comprising molybdenum complexed to a polybenzimidazole porous resin (PBI.Mo) was prepared using the following procedure (see Scheme 1):

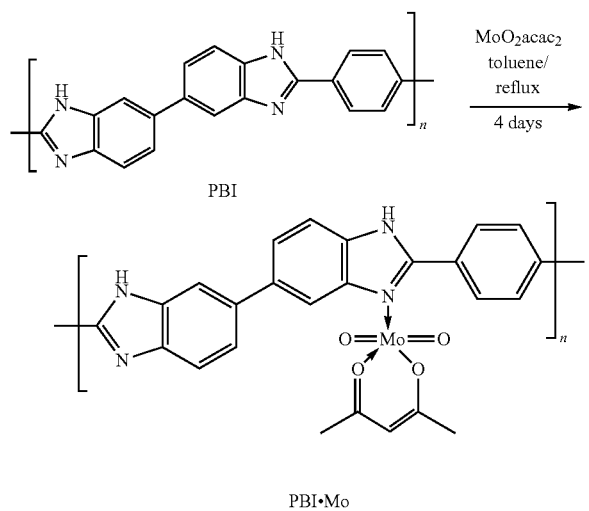

Scheme 1. Synthesis of PBI•Mo 10 g of wet polybenzimidazole porous resin beads, AUROREZ (trade mark, Hoechst-Celanese) was stirred with 1 M sodium hydroxide solution overnight, washed with deionised water until pH=7, washed with acetone and then dried under vacuum at 40° C. The nitrogen content of the resin was then determined by microanalysis to be 15.10% which, given that there are two nitrogen atoms in each imidazole repeat unit in the polymer, gives a ligand (imidazole) loading on the polymer of 5.39 mmol $g^{-1}$.

Typically for the synthesis of the PBI.Mo catalyst 5 g of the above resin (0.027 mol imidazole group) was refluxed with molybdenum acetylacetonate $MoO_2(acac)_2$ (17.68 g, 0.054 mol Mo) in anhydrous toluene for a period of four days. The resin beads changed colour from brown to green. The resulting catalyst composition was collected by filtration and then extracted with acetone in a Soxhlet apparatus for 48 hours. During extraction a dark blue colour was evident in the extracting solution, which disappeared eventually upon repeated introduction of fresh colourless solvent. The catalyst beads were then dried in a vacuum oven at 40° C.

Following grinding of a small sample of the PBI.Mo catalyst and dissolution in aqua regia, the resultant solution was made up with water before analysis by atomic absorption spectroscopy. From five replicate separate PBI.Mo catalyst preparations this yielded an average value for the Mo content of the catalyst of 0.95 mmol Mo $g^{-1}$. The corresponding average ligand (imidazole) loading from elemental microanalysis was 2.03 mmol $g^{-1}$, giving an average ligand:Mo mole ratio of 2.4:1.

The catalyst composition was activated prior to use in epoxiation reactions by refluxing with tert-butyl hydroperoxide in 1,2-dichloroethane using a mole ratio of Mo:tBHP of 1:80 during which the catalyst beads turned a yellow colour. When not in use the activated catalyst compositions were stored in a closed jar.

Particle size distribution measurement of the catalysts was carried out using Malvern Mastersizer. BET surface area measurements were carried out by the nitrogen adsorption and desorption method using a Micromeritics ASAP 2010 (Accelerated Surface Area and Porosimetry). The metal loading data, corresponding ligand/metal ratio and physical properties of polymer-supported Mo (VI) catalysts are presented in Table 1.

TABLE 1

Mo loading and Mo/ligand ratio and physical properties of polymer-supported Mo catalyst

| Properties | PBI.Mo catalyst |
| --- | --- |
| Mo loading (mmol Mo/g resin)[a] | 0.95 |
| Ligand loading mmol/g resin[b] | 2.3 |
| Ligand/Mo ratio | 2.4:1 |
| Particle size | 10% below 228 μm; 90% below 331 μm |
| BET surface area | 22.12 (±0.3) $m^2/g$ |

[a]From AAS analysis of digested resins.
[b]From N % elemental analysis of Mo loaded resins assuming ligand = imidazole or aminomethyl pyridine as appropriate.

Preparation of tert-butyl Hydroperoxide (TBHP)

t-Butyl hydroperoxide (70%) from the Aldrich Chemical Co. was rendered anhydrous by Dean-Stark distillation from a toluene solution following the modified method that was previously reported by Sharpless and Verhoeven [Sharpless, K. B.; Verhoeven, Aldrichim. Acta 12 (1979) 63.]. The molarity of TBHP was determined by iodimetry. The concentration of the TBHP in toluene was found to be 3.65 mol/$dm^3$.

GC Analysis

All the reactant and product compositions were analysed by gas chromatography. HP 5080 II Gas Chromatograph (GC) was used to analyse the composition of samples from the liquid phase of the reactive mixture.

The GC was fitted with a 30 m long J&W DB-5 MS, 0.32 mm diameter and 0.25 μm film capillary column with an FID detector. Both injector and detector temperatures were set at 473 K and helium carrier gas flow maintained at 1 ml/min (split ratio 100). For cyclohexene epoxidation column temperature was programmed between 313 and 473 K (313 K for 4.5 min, then ramp 25 K/min until 473 K). The sample size for GC was 0.4 μL and a complete GC run took about 11 min.

For the epoxidation of limonene column temperature was programmed between 323 and 473 K (323 K for 5 min, then ramped 4 K/min until 388 K and finally ramped 30 K/min until 473 K). The sample size for GC was 0.3 μL and a complete GC run took about 25 min (split ratio 100).

Preparation of the Catalyst Packing

Two mesh sheets, typically of the same size, were cut out of larger mesh sheet(s). The two sheets of mesh were initially joined together by soldering along three edges.

Figure 2:
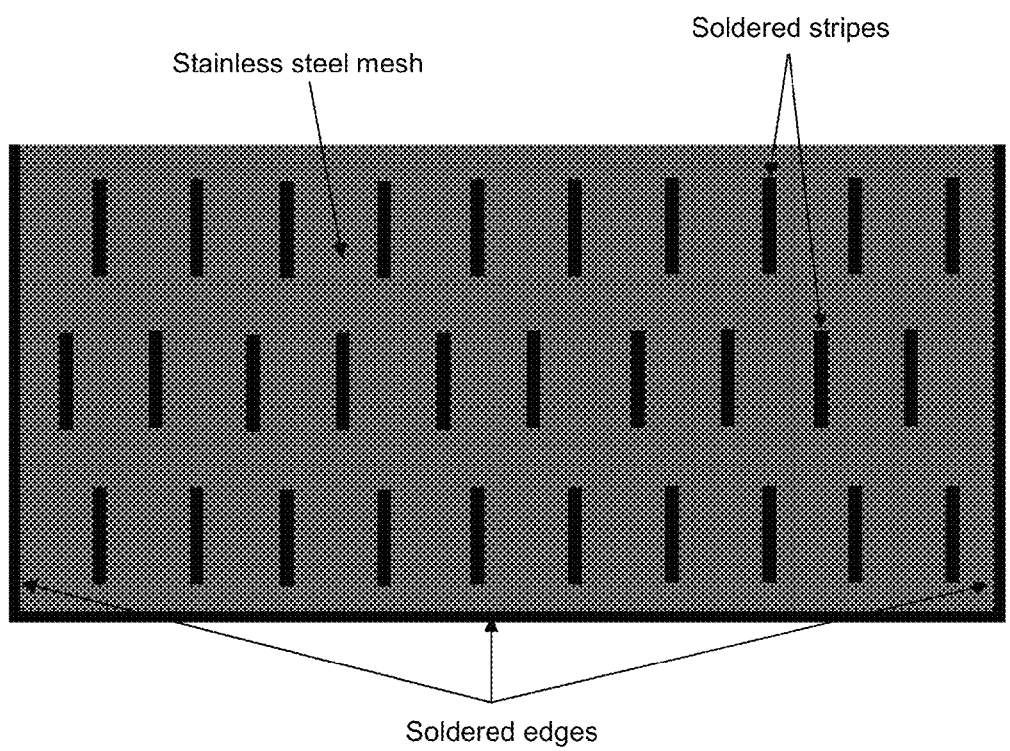
Figure 2:
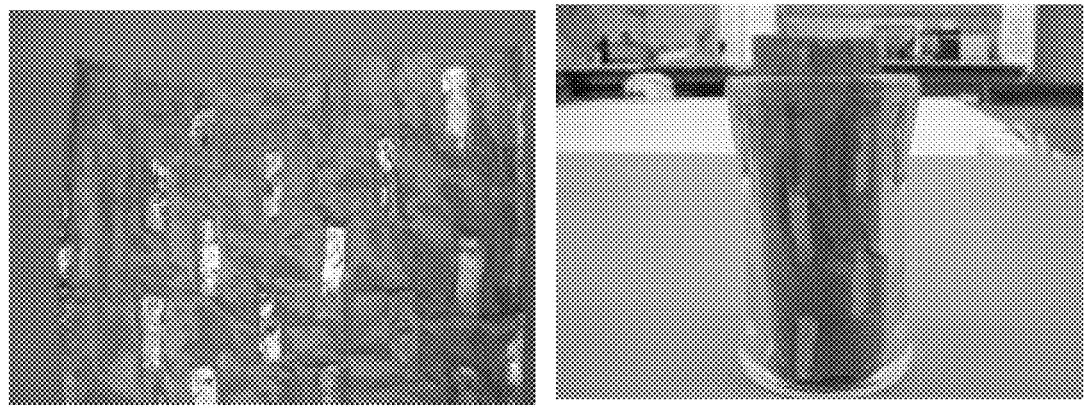

Then solder stripes were added by soldering through two layers of the mesh, joining two sides of the belt. The stripes were placed in a pattern within a distance of 0.03 m from each other in one line as shown in FIG. 2. The catalyst (50 g) was then placed between the two layers of mesh and the remaining edge was then soldered to seal the layers of mesh together. The same effect could be obtained by folding a single mesh sheet and soldering two edges before adding 50 g of the catalyst and then sealing the remaining edge. The catalyst containing belt was rolled up and placed into the reactive section of the column.

Typical Epoxidation Procedure

Cyclohexene and TBHP solution in toluene were weighted and introduced into the reboiler at an appropriate molar ratio. The reaction mixture was heated by steam circulated through the coil of the reboiler or by an oil bath. Once the temperature recorded by thermocouples placed along the column achieved the steady state, the column was heated for 1 hour. The temperature of the liquid recorded at the bottom and top of reactive section was 71° C. and the temperature of the vapour was 74° C. The reactants were fed in through the inlet ports, with the oxidant inlet port positioned above the reactive section and the olefin inlet port positioned below the reactive section, maintaining the same mole ratio of cyclohexene to TBHP as was used in the reboiler. Once the reactants were being pumped into the column, product withdrawal from the bottom of the reboiler was started, maintaining the same flow rate as that used to introduce the reactants into the column. After one hour of feeding the reactants into the column, samples were taken from the reboiler and other locations of the column for analysis. The process was continued for another hour and samples were withdrawn periodically for analysis and finally the process was stopped. Once the column was cooled, the liquid from the reboiler was drained and analysed.

All the chemicals used for this study were purchased from Aldrich Chemical Company Inc. and they were used without further purification.

Epoxidation of Cyclohexene in Reactive Distillation Column

For the lowest studied cyclohexene:TBHP mole ratio of 1.5:1, 80% TBHP conversion was achieved. Further increase of cyclohexene:TBHP ratios to 2:1, 2.5:1, 3:1 and 3.5:1 increased the TBHP conversion to 86% 90% 91% and 95%, respectively. The optimum conversion of TBHP (95%) was obtained for 3.5:1 cyclohexene:TBHP mole ratio. Increase of reaction rate and TBHP conversion with an increase in cyclohexene:TBHP mole ratio was already found in batch studies carried out in our earlier work. However, for continuous epoxidation in the RDC the increase of cyclohexene:TBHP mole ratio above that optimal ratio (3.5:1) resulted in slight reduction of TBHP conversion. It can be seen that for cyclohexene:TBHP mole ratio of 5.5:1, TBHP conversion dropped to 92%. At very high mole ratio of cyclohexene:TBHP, because of relatively low boiling point (82° C.) and high volatility of cyclohexene the reflux in the column was very vigorous and most of the unreacted cyclohexene reached the top of the RDC. Because of vigorous reflux in the column the residence time of the reactants in the reactive section of the column was reduced substantially, which resulted in lower TBHP conversion for very high contents of cyclohexene in the RDC. It is to be noted that for cyclohexene:TBHP mole ratio of above 5.5:1 the column had significant flooding.

Figure 4:
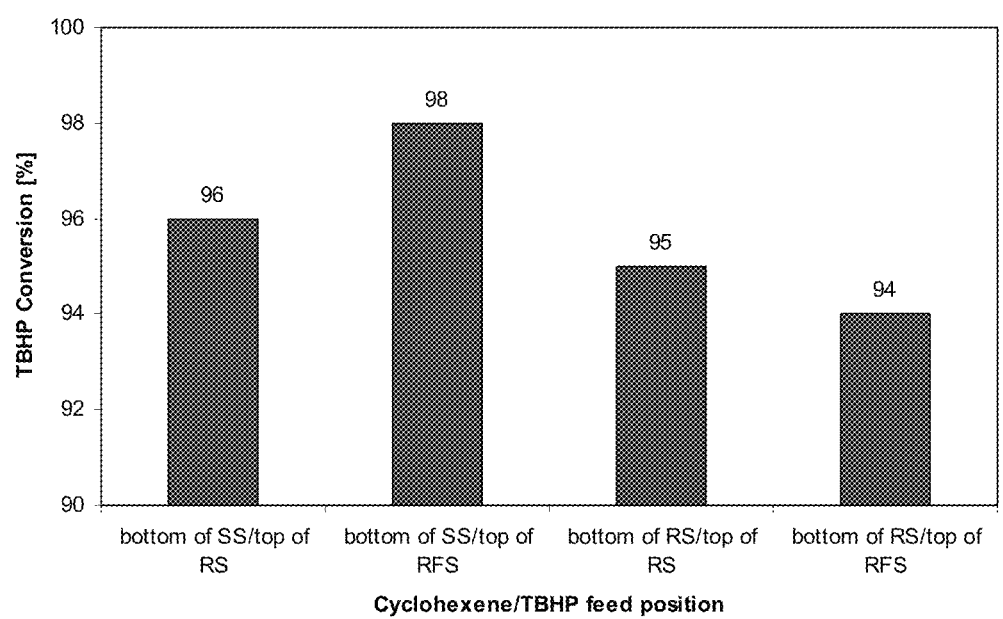
FIG. 4 shows the percentage conversion of TBHP for cyclohexene epoxidation in the process of the present invention using the reactive distillation column relative to the feed positions on the column.

The column was designed in a way to allow feed substrates at four different locations i.e. bottom of the stripping section (SS), bottom of the reactive section (RS), top of the reactive section (RS), and top of the rectifying section (RFS). The boiling point of the solution of TBHP in toluene is higher than cyclohexene and therefore TBHP was fed above the cyclohexene feed point in the RDC. Apart from standard feed position (TBHP at the top of the RS, cyclohexene at the bottom of the RS) used in the feed mole ratio runs we studied three other possible positions. For all feed position experiments cyclohexene:TBHP ratio of 3.5:1 was employed. As shown in FIG. 4 the THBP conversion for standard experiment was already high (95%) the differences in conversion for other feed position have not been significant. However, the highest TBHP conversion (98%) was obtained when TBHP was fed at the top of the rectifying section and cyclohexene was introduced at the bottom of the striping section. These feed positions are the two most distant possible feeding points.

In feed mole ratio and feed position studies we used TBHP flow rate of 1 ml/min. For this flow rate 98% TBHP conversion was obtained.

Figure 5:
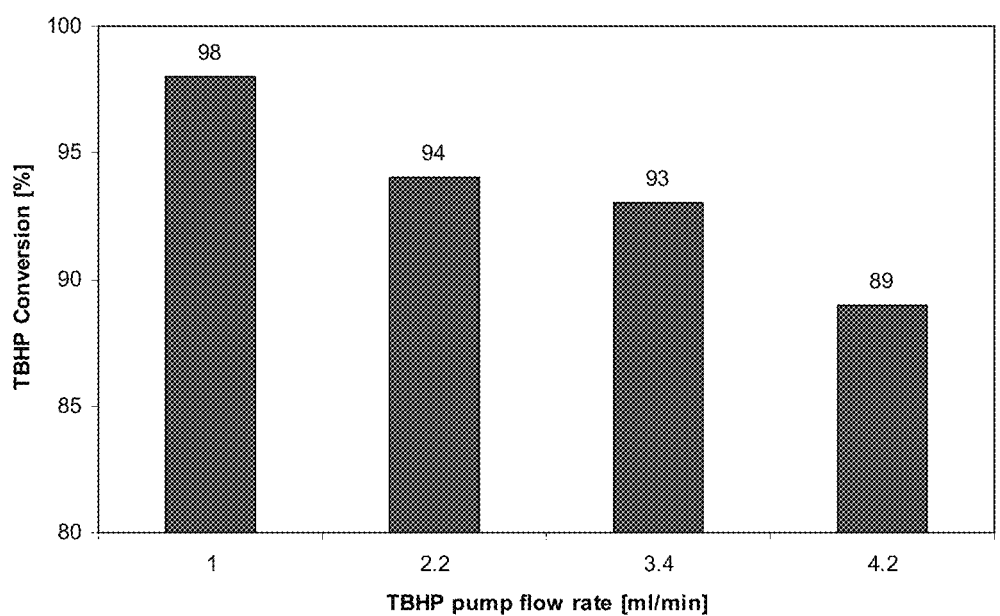
FIG. 5 shows the TBHP conversions in the process of the present invention using the reactive distillation column relative to the flow rate of the reagents into the column.

It is shown in FIG. 5 that the increase of TBHP flow rate reduced TBHP conversion. To keep the same reactants mole ratio both TBHP and cyclohexene flow rate were increased. However, the flow rate of TBHP is important because it is the limiting reactant for this system. Increasing the TBHP flow rate to 2.2 and then 3.4 ml/min slightly reduced the TBHP conversion to 94% and 93%, respectively. Further increase of TBHP flow rate to 4.2 ml/min decreased the TBHP conversion almost by 10% compared to the lowest TBHP flow rate of 1 ml/min.

Epoxidation of Limonene in Reactive Distillation Column

Figure 6:
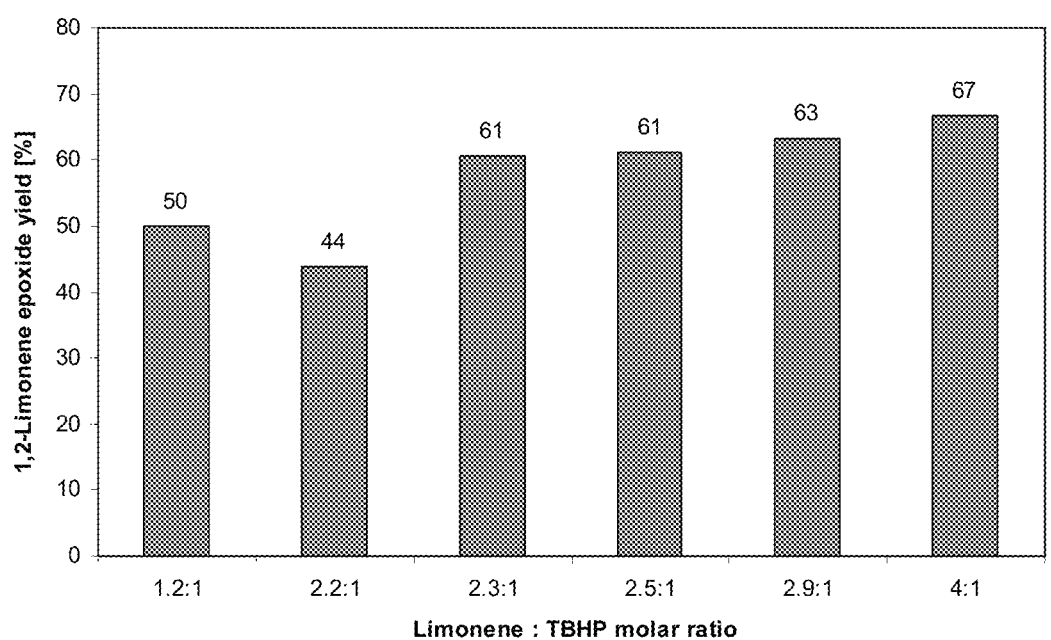
FIG. 6 shows the percentage yield of 1,2-limonene epoxide in the process of the present invention using the reactive distillation column dependant on the ratios of limonene to oxidant.

Similar optimisation studies as those performed on cyclohexne were performed using limonene as the olefin. It can be seen from FIG. 6, that the best conversions to the epoxide were achieved when using a ratio of olefin to oxidant of 4:1.

Figure 7:
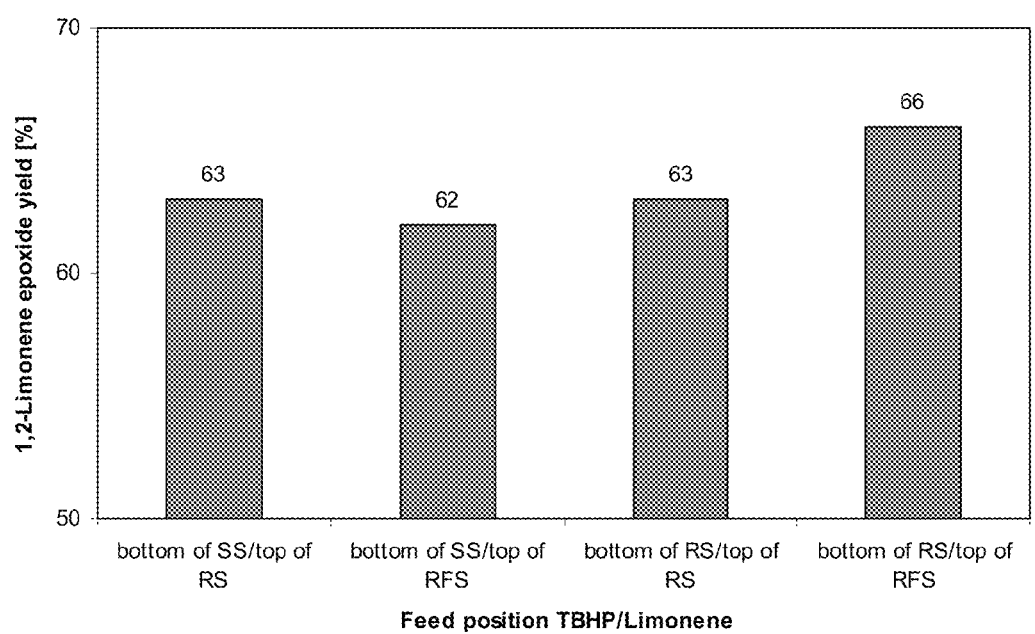
FIG. 7 shows the percentage yield of 1,2-limonene epoxide in the process of the present invention using the reactive distillation column relative to the feed positions on the column.

It can also be seen in FIG. 7 that the optimum positions for the inlet ports when limonene is used as the olefin is when the TBHP is introduced at the bottom of the reactive section and limonene is introduced at the top of the rectifying section.

The invention claimed is:

1. A permeable particle container comprising two sheets of mesh, or one sheet of mesh folded, sealed by solder along the edges, leaving one edge open to allow for the addition of particulate material, which edge is solderable to seal the particle container, wherein the mesh has flexibility that allows the container to be rolled; wherein the particle container comprises soldered stripes that are from 1 to 3 cm apart and positioned so that their longer side is parallel to the shorter side of the container and wherein the length of each stripe is less than the length of the short side of the container.

2. A container according to claim 1, wherein the stripes are about 0.005 m wide and about 0.020 to 0.025 m in length.

3. A container according to claim 1, wherein the mesh size is less than 0.1 mm.

4. A container according to claim 3, wherein the mesh size is from about 0.01 mm to about 0.05 mm.

5. A container according to claim 1, wherein the particulate material is a catalyst.

6. A container according to claim 5 wherein the catalyst is an epoxidation catalyst.

* * * * *

UNITED STATES PATENT AND TRADEMARK OFFICE
CERTIFICATE OF CORRECTION

| | | |
|---|---|---|
| PATENT NO. | : 9,248,942 B2 | Page 1 of 1 |
| APPLICATION NO. | : 14/277335 | |
| DATED | : February 2, 2016 | |
| INVENTOR(S) | : Basudeb Saha et al. | |

It is certified that error appears in the above-identified patent and that said Letters Patent is hereby corrected as shown below:

On the title page item (30), Foreign Application Priority Data, please insert:
--Jul. 31, 2009  (GB) ..................... 0913318.2--

Signed and Sealed this
Nineteenth Day of April, 2016

Michelle K. Lee
*Director of the United States Patent and Trademark Office*